(12) United States Patent  (10) Patent No.: US 8,025,841 B2
Lambert et al.  (45) Date of Patent: Sep. 27, 2011

(54) METHOD OF STERILIZING AN ORTHOPAEDIC IMPLANT

(75) Inventors: Richard D. Lambert, Germantown, TN (US); Terry W. McLean, Cordova, TN (US); David B. Vogel, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/017,943

(22) Filed: Jan. 31, 2011

(65) Prior Publication Data

US 2011/0123395 A1    May 26, 2011

Related U.S. Application Data

(60) Continuation of application No. 11/615,127, filed on Dec. 22, 2006, now Pat. No. 7,947,220, which is a division of application No. 10/914,551, filed on Aug. 9, 2004.

(60) Provisional application No. 60/493,247, filed on Aug. 7, 2003.

(51) Int. Cl.
| | |
|---|---|
| A61L 2/08 | (2006.01) |
| A61L 9/00 | (2006.01) |
| A61L 2/00 | (2006.01) |
| B08B 9/00 | (2006.01) |
| B08B 3/00 | (2006.01) |
| A61F 2/32 | (2006.01) |
| A61F 2/60 | (2006.01) |
| A61F 2/80 | (2006.01) |
| A61F 2/24 | (2006.01) |
| A61F 5/00 | (2006.01) |
| A61B 17/56 | (2006.01) |

(52) U.S. Cl. .................. 422/28; 422/1; 422/26; 422/32; 422/34; 422/305; 422/36; 422/37; 134/22.15; 134/30; 134/31; 623/22.21; 623/22.245; 623/22.25; 623/22.32; 623/22.38; 623/22.39; 623/22.42; 623/22.43; 623/22.13; 623/22.34; 623/22.35; 623/920; 623/923; 623/11.11; 623/66.1; 606/53; 606/56; 606/249; 606/302; 606/303; 606/304; 606/91

(58) Field of Classification Search ................ 422/1, 26, 422/28, 32, 34, 298, 305, 36–37; 134/22.15, 134/30–31; 623/920, 923, 11.11–66.1; 606/53, 606/56, 249, 302–304, 91
See application file for complete search history.

(56) References Cited

U.S. PATENT DOCUMENTS 3,608,096 A    9/1971  Link
(Continued)

FOREIGN PATENT DOCUMENTS

EP    1369094    12/2003
(Continued)

OTHER PUBLICATIONS

Office Action dated Feb. 8, 2006 in U.S. Appl. No. 10/914,551.
(Continued)

*Primary Examiner* — Jill Warden
*Assistant Examiner* — Monzer Chorbaji
(74) *Attorney, Agent, or Firm* — Kilpatrick Townsend & Stockton LLP

(57) ABSTRACT

A pre-assembled orthopaedic implant adapted for improved gas sterilization. The implant includes a first component adapted for assembly with a second component such that a mating surface of the first component is in close proximity with a mating surface of the second component. At least one gas conduit associated with the mating surface of the first component facilitates a sterilizing gas to penetrate into and dissipate from the interface defined by the mating surfaces.

18 Claims, 3 Drawing Sheets

U.S. PATENT DOCUMENTS

| | | | |
|---|---|---|---|
| 3,818,514 A | 6/1974 | Clark |
| 3,840,904 A | 10/1974 | Tronzo |
| 3,882,550 A | 5/1975 | Karpf et al. |
| 3,903,549 A | 9/1975 | Deyerle |
| 4,550,546 A | 11/1985 | Raley et al. |
| 4,664,058 A | 5/1987 | Schroeder et al. |
| 4,714,477 A | 12/1987 | Fichera et al. |
| 4,976,731 A | 12/1990 | Perry |
| 5,019,105 A | 5/1991 | Wiley |
| 5,059,209 A | 10/1991 | Jones |
| 5,080,677 A | 1/1992 | Shelley |
| RE33,854 E | 3/1992 | Adair |
| 5,139,497 A | 8/1992 | Tilghman et al. |
| 5,246,462 A | 9/1993 | Bekki et al. |
| 5,350,300 A | 9/1994 | Gallais |
| 5,480,448 A | 1/1996 | Mikhail |
| 5,547,635 A | 8/1996 | Duthie, Jr. |
| 5,577,368 A | 11/1996 | Hamilton et al. |
| 5,641,323 A | 6/1997 | Caldarise |
| 5,681,322 A | 10/1997 | Hartigan, Jr. |
| 5,702,476 A | 12/1997 | Limacher et al. |
| 5,716,413 A | 2/1998 | Walter et al. |
| 5,732,821 A | 3/1998 | Stone et al. |
| 5,782,927 A | 7/1998 | Klawitter et al. |
| 6,110,205 A | 8/2000 | Nies |
| 6,152,962 A | 11/2000 | DeCarlo, Jr. |
| 6,242,507 B1 | 6/2001 | Saum et al. |
| 6,268,048 B1 | 7/2001 | Topolkaraev et al. |
| 6,403,033 B1 | 6/2002 | Gutman |
| 6,500,386 B1 | 12/2002 | Burstein |
| 6,889,839 B1 | 5/2005 | Rosten et al. |
| 6,986,792 B2 | 1/2006 | McLean et al. |
| 7,302,784 B2 | 12/2007 | Harges et al. |
| 2002/0068980 A1 | 6/2002 | Serbousek et al. |
| 2002/0120342 A1 | 8/2002 | Gibbs |
| 2002/0168289 A1 | 11/2002 | McVey |
| 2003/0009230 A1 | 1/2003 | Gundlapalli et al. |
| 2003/0114935 A1 | 6/2003 | Chan et al. |
| 2003/0177819 A1 | 9/2003 | Maale |
| 2004/0019380 A1 | 1/2004 | Baege et al. |
| 2005/0102033 A1 | 5/2005 | Lambert |
| 2005/0261777 A1 | 11/2005 | Jones et al. |
| 2006/0149285 A1 | 7/2006 | Burgi et al. |
| 2007/0088442 A1 | 4/2007 | Cima et al. |
| 2007/0122305 A1 | 5/2007 | Lambert et al. |
| 2007/0219412 A1 | 9/2007 | DiGiovanni et al. |
| 2007/0249899 A1 | 10/2007 | Seifert |

FOREIGN PATENT DOCUMENTS

| | | |
|---|---|---|
| JP | 1221164 | 9/1989 |
| JP | 04044756 | 2/1992 |
| WO | WO9959500 | 11/1999 |
| WO | WO03049930 | 6/2003 |
| WO | WO2005013865 | 2/2005 |
| WO | WO2008100541 | 2/2008 |

OTHER PUBLICATIONS

Response dated Jun. 8, 2006 in U.S. Appl. No. 10/914,551.
Office Action dated Nov. 6, 2006 in U.S. Appl. No. 10/914,551.
Response dated Feb. 1, 2007 in U.S. Appl. No. 10/914,551.
Advisory Action dated Feb. 27, 2007 in U.S. Appl. No. 10/914,551.
Response dated Apr. 5, 2007 in U.S. Appl. No. 10/914,551.
Office Action dated Jun. 19, 2007 in U.S. Appl. No. 10/914,551.
Response dated Nov. 15, 2007 in U.S. Appl. No. 10/914,551.
Office Action dated Feb. 28, 2008 in U.S. Appl. No. 10/914,551.
Response dated May 28, 2008 in U.S. Appl. No. 10/914,551.
Office Action dated Aug. 27, 2008 in U.S. Appl. No. 10/914,551.
Response dated Dec. 23, 2008 in U.S. Appl. No. 10/914,551.
Office Action dated Mar. 10, 2009 in U.S. Appl. No. 10/914,551.
Pre-Appeal Conference Request dated Jul. 10, 2009 in U.S. Appl. No. 10/914,551.
Pre-Appeal Conference Decision dated Sep. 8, 2009 in U.S. Appl. No. 10/914,551.
Office Action dated Nov. 6, 2009 in U.S. Appl. No. 10/914,551.
Response dated Feb. 8, 2010 in U.S. Appl. No. 10/914,551.
Office Action dated May 12, 2010 in U.S. Appl. No. 10/914,551.
Response dated Sep. 10, 2010 in U.S. Appl. No. 10/914,551.
Notice of Allowance dated Sep. 23, 2010 in U.S. Appl. No. 10/914,551.
Response dated Oct. 19, 2010 in U.S. Appl. No. 10/914,551.
Notice of Allowability dated Oct. 26, 2010 in U.S. Appl. No. 10/914,551.
Request for Continued Examination dated Dec. 16, 2010 in U.S. Appl. No. 10/914,551.
Office Action dated May 27, 2010 in U.S. Appl. No. 11/615,127.
Response dated Jun. 28, 2010 in U.S. Appl. No. 11/615,127.
Office Action dated Sep. 15, 2010 in U.S. Appl. No. 11/615,127.
Response dated Dec. 15, 2010 in U.S. Appl. No. 11/615,127.
Notice of Allowance dated Jan. 21, 2011 in U.S. Appl. No. 11/615,127.
Sigholm, et al., "Graft Perforations Favor Osteoinduction, Studies of Rabbit Cortical Grafts Sterilized with Ethylene Oxide," *Acta Orthop. Scand.*, 63(2):177-182 (1992).

METHOD OF STERILIZING AN ORTHOPAEDIC IMPLANT

CROSS-REFERENCE TO RELATED APPLICATIONS

This application is a continuation of U.S. patent application Ser. No. 11/615,127 filed on Dec. 22, 2006, which is a divisional of U.S. patent application Ser. No. 10/914,551 filed on Aug. 9, 2004, which claims the benefit of U.S. Provisional Application No. 60/493,247, filed Aug. 7, 2003 and entitled "Modified Orthopaedic Implants for Improved Sterilization." The disclosure of each application is incorporated by reference in its entirety.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

Embodiments of the present invention relate to pre-assembled orthopaedic implants adapted for gas sterilization.

2. Related Art

Orthopaedic implants, such as knee, hip or shoulder prostheses, occasionally include components that are shipped to the surgeon or other user in a pre-assembled condition. For example, a hip prosthesis may include a bipolar component that includes a metal acetabular shell pre-assembled with a plastic liner. To lessen the chances of post-implantation failure, the shell and liner must fit together snugly, with a relatively tight interface between the two components.

Pre-assembled components, as well as other orthopaedic implant components, may be sterilized prior to use to minimize the chances of infection. Orthopaedic components may be sterilized using a number of different techniques, including gas sterilization and gamma radiation.

In some circumstances, gas sterilization is a preferred technique for sterilizing orthopaedic components. Gas sterilization utilizes a gas such as ethylene oxide (ETO) or vaporized hydrogen peroxide (VHP) to incapacitate bacterial or other disease causing agents. However, gas sterilization may be ineffective in certain circumstances. For example, if during sterilization the gas is unable to contact all surfaces of the orthopaedic components, it may not effectively sterilize those components.

Typical pre-assembled orthopaedic components may not be suitable for gas sterilization. Because of the relatively tight interface between the components, the gas may not be able to penetrate between the components to sterilize all of the surfaces. Additionally, even if some of the gas penetrates between the pre-assembled components, the gas may not necessarily be able to effectively dissipate from in between the tightly fitted pre-assembled components after sterilization is complete. Trace amounts of gas may remain in the implant, potentially having deleterious effects on the health of the individual who receives the implant.

Because typical pre-assembled orthopaedic implants may not be suitable for gas sterilization, they have in the past been sterilized using the less preferable gamma irradiation technique. Gamma irradiation may cause oxidation of plastics, such as the polyethylene commonly used for the plastic liner of a pre-assembled orthopaedic component. Oxidation of the polyethylene forming the plastic liner may weaken the component, increasing the chance that the implant will fail. Gamma irradiation may also be undesirable because it may neutralize the effects of cross-linking in highly cross-linked plastic components, also potentially weakening the component.

SUMMARY OF THE INVENTION

Various embodiments of the present invention include a pre-assembled orthopaedic implant suitable for gas sterilization. In some embodiments, one or more gas conduits associated with one or more of the orthopaedic components facilitates the penetration and/or dispersion of a sterilizing gas into and from the pre-assembled components, but do not affect the mechanical integrity or overall performance of the implant. Embodiments of the present invention may include pre-assembled knee, hip, shoulder or other orthopaedic components.

In accordance with embodiments of the present invention, the gas conduit or conduits may be formed in several suitable shapes, sizes, locations, orientations or configurations. For example, in some embodiments the gas conduits are a plurality of channels inscribed onto a mating surface of one or more of the orthopaedic components. In other embodiments, the gas conduits are one or more apertures passing through one or more of the orthopaedic components. Other embodiments may include any combination of the foregoing gas conduits, or other structures serving as suitable gas conduits.

Further features, aspects, and advantages of the present invention, as well as the structure and operation of various embodiments of the present invention, are described in detail below with reference to the accompanying drawings.

DETAILED DESCRIPTION OF THE EMBODIMENTS

Figure 1:
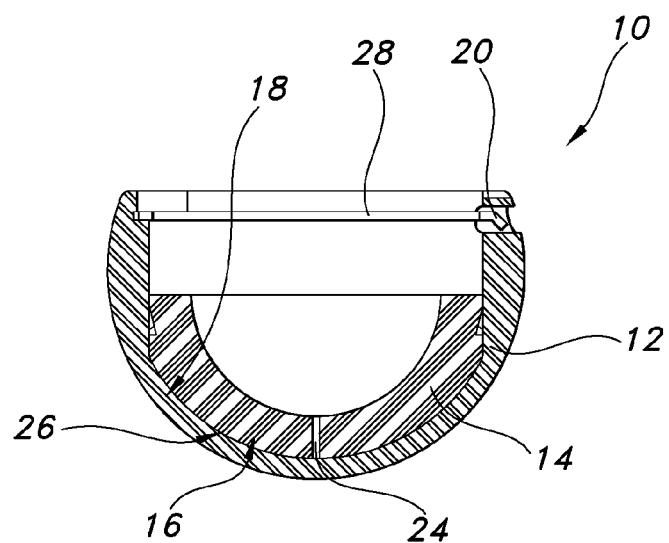
FIG. 1 shows a schematic cross-sectional view of a orthopaedic implant shown in a pre-assembled condition in accordance with a first embodiment of the present invention.
Figure 5:
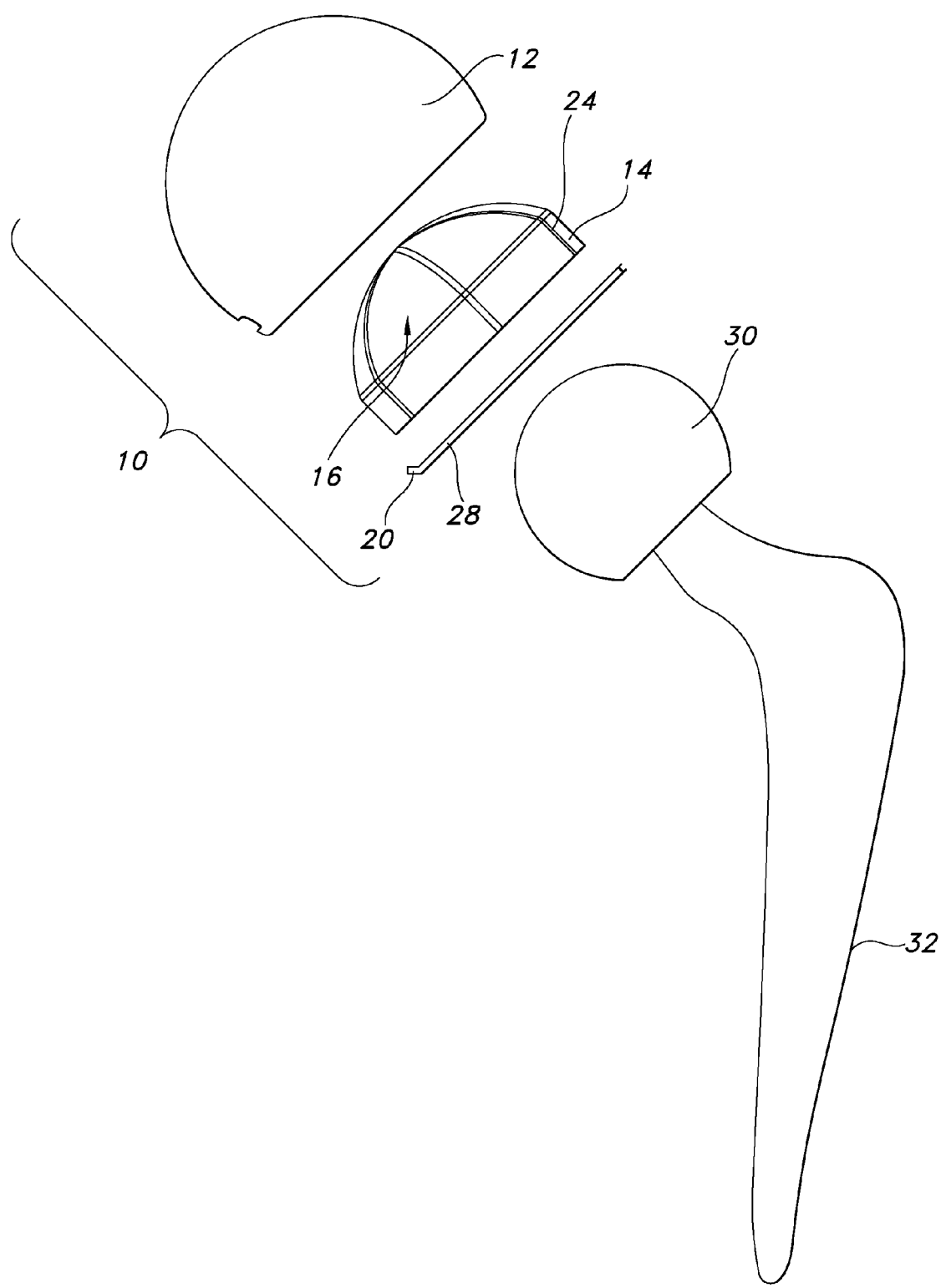
FIG. 5 shows a schematic view of an orthopaedic hip implant in accordance with another embodiment of the present invention, shown in a disassembled state.

Referring to the accompanying drawings in which like reference numbers indicate like elements, FIG. 1 shows an orthopaedic implant 10 according to a first embodiment of the present invention. The implant 10 shown in FIG. 1 is adapted for implantation into the acetabulum of a hip such that the implant 10 can receive a prosthetic femoral head in a rotating fashion (however, embodiments of the present invention also include implants that can interact with natural portions of the anatomy—such as natural femoral heads). FIG. 5 shows (in a disassembled state) implant 10 associated with a femoral head 30 and stem 32.

As shown in FIG. 1, orthopaedic implants 10 in accordance with embodiments of the present invention may include at least two orthopaedic components 12 and 14. FIG. 1 shows the implant including two components: an acetabular shell 12 and a liner 14. In the embodiment shown in FIG. 1, acetabular shell 12 is metal and liner 14 is a plastic, such as ultra high molecular weight polyethylene. However, shell 12 and liner 14 may be formed from any desirable material.

Implant 10 may be assembled by press fitting liner 14 into an interior cavity of acetabular shell 12 such that a mating surface 16 on the liner 14 is in close proximity with a mating surface 18 of the acetabular shell 12, defining a mating surface interface 26. Liner 14 may be secured in shell 12 in any desirable, conventional, or non-conventional manner.

Implant 10 may be shipped with the liner 14 assembled in the shell 12 and may be sterilized after assembly. If necessary or desired, the pre-assembled implant 10 may be later combined with other components to finalize assembly of the implant prior to implantation. A retaining ring 28 may secure the additional component to the pre-assembled implant.

Pre-assembled implant 10 may include one or more gas conduits 24. Gas conduits 24, as discussed above, may permit sterilization gasses such as ETO or VHP to penetrate into the mating surface interface 26, between the mating surfaces 16 and 18 of the shell 12 and liner 14. Gas conduits 24 may also facilitate dispersion of the sterilization gas from in-between the mating surfaces 16 and 18 of the components after sterilization is complete. Gas conduits 24 may be formed as one or more channels, one or more apertures, any combination of channels and apertures, or any other desired structure. The gas conduits 24 may be formed by machining, molding or any other conventional or non-conventional technique.

Figure 2:
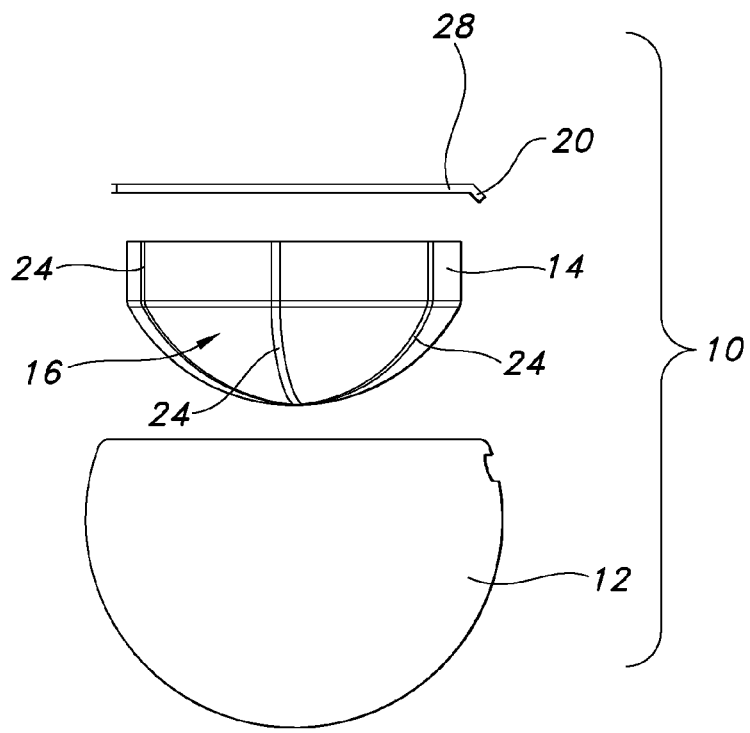
FIG. 2 shows a schematic view of the pre-assembled orthopaedic implant shown in FIG. 1 in a disassembled condition.

FIG. 1 shows an aperture gas conduit 24 extending from an inner surface to the outer, mating surface 16 of the liner. FIG. 2 shows a plurality of channel gas conduits 24 engraved in the mating surface 16 of the liner. In some embodiments, the liner may include both channels and apertures as gas conduits.

Figure 4:
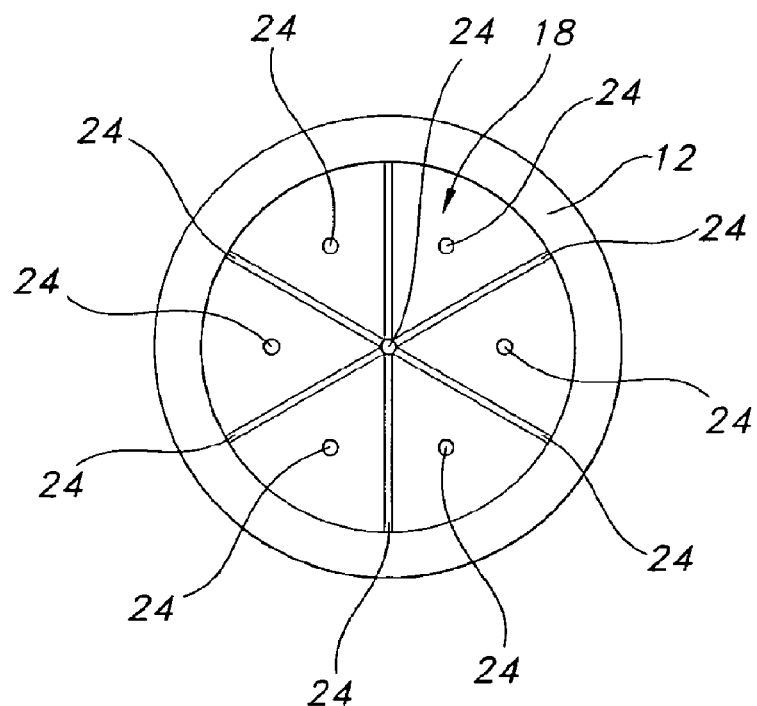
FIG. 4 shows a schematic view of an orthopaedic component in accordance with another embodiment of the present invention.

In still other embodiments, such as the embodiment shown in FIG. 4, the acetabular shell 12 may also include gas conduits 24, such as apertures and channels. Gas conduits 24 associated with the acetabular shell 12 may facilitate the penetration and subsequent dispersion of sterilizing gas in a similar manner to gas conduits 24 associated with the liner 14.

Figure 3:
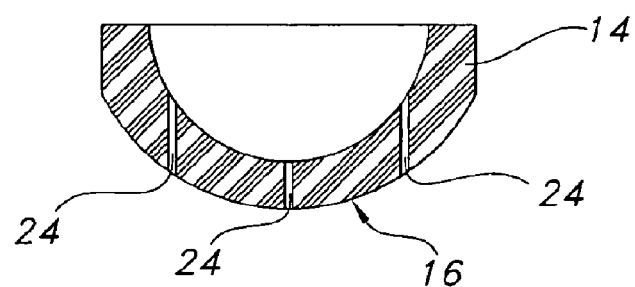
FIG. 3 shows a schematic cross-sectional view of an orthopaedic component in accordance with another embodiment of the present invention.

Gas conduits 24 may be associated with the shell 12, liner 14, or both, in any desired number, position or orientation to maximize the facilitation of penetration and dispersion of sterilizing gas between the mating surfaces 16 and 18 of the acetabular shell 12 and liner 14. For example, in the embodiment shown in FIGS. 1 and 2, the acetabular liner 14 includes three channels forming arcs on the surface of the liner 14 and one aperture at an apex of the liner 14. Alternatively, as the embodiment in FIG. 3 shows, there are multiple apertures extending through the acetabular liner 14. In the alternate embodiment shown in FIG. 4, multiple channels and multiple apertures are associated with the acetabular shell 14.

As those skilled in the art will appreciate, the particular embodiment of this invention described above and illustrated in the figures is provided for explaining the invention, and various alterations may be made in the structure and materials of the illustrated embodiment without departing from the spirit and scope of the invention as described above. For example, orthopaedic implants in accordance with the present invention are not limited to acetabular shells and liners. Pre-assembled implants for use with knees, shoulders or other joints of the anatomy may also include gas conduits for improved sterilization in accordance with the embodiments of the present invention.

What is claimed is:

1. A method of sterilizing an orthopaedic implant comprising the step of subjecting the orthopaedic implant to a sterilization gas when the orthopaedic implant is in a pre-assembled condition, wherein the pre-assembled condition comprises:
   a first orthopaedic implant that has been press-fitted into a second orthopaedic implant such that the first orthopaedic implant is seated in the second orthopaedic implant so that a first mating surface of the first orthopaedic implant confronts a second mating surface of the second orthopaedic implant to define a mating surface interface;
   wherein at least one of the first and second orthopaedic implants comprises an articular surface opposite the mating surface of the at least one first and second orthopaedic implant;
   wherein at least one of the first and second mating surfaces comprises a plurality of gas channels formed therein; and wherein at least some of the plurality of gas channels intersect proximate an apex of the at least one of the first and second mating surfaces.

2. The method of claim 1, wherein subjecting the orthopaedic implant to the sterilization gas further comprises, when in the pre-assembled condition, at least one of the first and second orthopaedic implants further comprising a gas conduit extending through the first or second orthopaedic implant.

3. The method of claim 1, wherein subjecting the orthopaedic implant to the sterilization gas further comprises, when in the pre-assembled condition, at least one of the first and second mating surfaces comprising a hemispherical shape having the apex.

4. The method of claim 3, wherein subjecting the orthopaedic implant to the sterilization gas further comprises, when in the pre-assembled condition, at least one of the first and second orthopaedic implants further comprising a gas conduit extending therethrough.

5. The method of claim 1, wherein subjecting the orthopaedic implant to the sterilization gas further comprises, when in the pre-assembled condition, at least one of the first and second mating surfaces defining a hemispherically shaped mating surface, wherein at least one of the plurality of gas channels circumscribes the hemispherically shaped mating surface and extends through the apex of the hemispherically shaped mating surface.

6. The method of claim 1, wherein subjecting the orthopaedic implant to the sterilization gas further comprises, when in the pre-assembled condition, the first orthopaedic implant comprising an acetabular liner and the second orthopaedic implant comprising an acetabular shell.

7. The method of claim 6, wherein subjecting the orthopaedic implant to the sterilization gas further comprises, when in the pre-assembled condition, the first mating surface defining an outer, substantially hemispherically shaped surface and the articular surface defining an inner, substantially hemispherically shaped surface.

8. The method of claim 1, wherein subjecting the orthopaedic implant to the sterilization gas further comprises, when in the pre-assembled condition, the articular surface defining a curved surface.

9. A method of sterilizing an orthopaedic implant, comprising the step of subjecting the orthopaedic implant to a sterilization gas when the orthopaedic implant is in a pre-assembled condition, wherein the pre-assembled condition comprises:

a first orthopaedic implant that has been assembled to a second orthopaedic implant such that a first mating surface of the first orthopaedic implant confronts a second mating surface of the second orthopaedic implant to define a mating surface interface;

wherein the first orthopaedic implant includes an articular surface opposite the first mating surface;

wherein the first mating surface includes a gas plurality of channels formed therein that extends along the mating surface interface; and wherein at least some of the plurality of gas channels formed in the first mating surface intersect proximate an apex of the first mating surface.

10. The method of claim 9, wherein subjecting the orthopaedic implant to the sterilization gas further comprises, when in the pre-assembled condition, the first mating surface being substantially hemispherically shaped and the second mating surface being substantially hemispherically shaped.

11. The method of claim 9, wherein subjecting the orthopaedic implant to the sterilization gas further comprises, when in the pre-assembled condition, at least some of the plurality of gas channels formed in the first mating surface intersecting proximate an apex of the second mating surface.

12. The method of claim 9, wherein subjecting the orthopaedic implant to the sterilization gas further comprises, when in the pre-assembled condition, the first orthopaedic implant further comprising at least one gas conduit aperture extending from the first mating surface to the articular surface.

13. The method of claim 12, wherein subjecting the orthopaedic implant to the sterilization gas further comprises, when in the pre-assembled condition, the first mating surface comprising a substantially hemispherical shape, wherein the at least one gas conduit aperture extends from the apex of the first mating surface.

14. The method of claim 9, wherein subjecting the orthopaedic implant to the sterilization gas in the pre-assembled condition further comprises, when in the pre-assembled condition, the plurality of gas channels formed in the first mating surface intersect proximate the apex of the first mating surface.

15. The method of claim 9, wherein subjecting the orthopaedic implant to the sterilization gas in the pre-assembled condition further comprises, when in the pre-assembled condition, the articular surface defining a curved surface.

16. A method of sterilizing an orthopaedic implant, comprising the step of subjecting the orthopaedic implant to a sterilization gas when the orthopaedic implant is in a pre-assembled condition, wherein the pre-assembled condition comprises:

a first orthopaedic implant that has been press-fitted into a second orthopaedic implant such that a substantially hemispherical first mating surface of the first orthopaedic implant confronts a substantially hemispherical second mating surface of the second orthopaedic implant to define a substantially hemispherical mating surface interface;

wherein the first orthopaedic implant includes an articular surface opposite the first mating surface; and wherein at least one of the first and second mating surfaces includes a plurality of gas channels formed therein that extend along the mating surface interface, wherein at least some of the gas channels intersect proximate an apex of the substantially hemispherical mating surface interface.

17. The method of claim 16, wherein subjecting the orthopaedic implant to the sterilization gas further comprises, when in the pre-assembled condition, at least one of the first and second orthopaedic implants comprise a plurality of gas apertures extending through the at least one of the first and second orthopaedic implants to the mating surface interface.

18. The method of claim 17, wherein subjecting the orthopaedic implant to the sterilization gas further comprises, when in the pre-assembled condition, the first orthopaedic implant comprising an acetabular liner and the second orthopaedic implant comprising an acetabular shell.

\* \* \* \* \*